United States Patent [19]

Reddy et al.

[11] Patent Number: 5,296,123
[45] Date of Patent: Mar. 22, 1994

[54] IN-TANK ELECTROCHEMICAL SENSOR

[75] Inventors: Vilambi N. R. k. Reddy, Lakewood; Frank A. Ludwig, Rancho Palos Verdes; Bruce M. Eliash; Nguyet H. Phan, both of Los Angeles, all of Calif.

[73] Assignee: Hughes Aircraft Company, Los Angeles, Calif.

[21] Appl. No.: 945,751

[22] Filed: Sep. 16, 1992

[51] Int. Cl.$^5$ ............................................. G01N 27/26
[52] U.S. Cl. .................. 204/153.1; 204/409; 204/412; 204/434
[58] Field of Search ............. 204/412, 434, 153.1, 204/DIG. 8, DIG. 9, 409, 232, 275; 205/101, 102, 103, 104, 105, 81

[56] References Cited

U.S. PATENT DOCUMENTS 4,496,454  1/1985  Berger ................................ 204/409
4,631,116 12/1986  Ludwig ............................... 204/434

Primary Examiner—John Niebling
Assistant Examiner—Bruce F. Bell
Attorney, Agent, or Firm—M. E. Lachman; M. W. Sales; W. K. Denson-Low

[57] ABSTRACT

An electrochemical sensor adapted for use in the electrochemical analysis of liquids. The sensor includes a cell assembly having a liquid flow control chamber, sensing chamber and liquid exit chamber. Liquids to be measured are pumped into the liquid flow control chamber where any turbulence in the liquid is dampened. The non-turbulent liquid is passed from the liquid flow control chamber to the sensing chamber. The sensing chamber includes a working electrode and a counter-electrode. The non-turbulent liquid is passed from the sensing chamber to the liquid exit chamber where it is contacted with a reference electrode. The liquid then exits the sensor. The sensor is well-suited for use in the electrochemical analysis of plating bath solutions where sub-milliampere type AC and DC voltammetric measurements are required in order to generate electrochemical spectra which are indicative of constituents present in the solution.

18 Claims, 3 Drawing Sheets

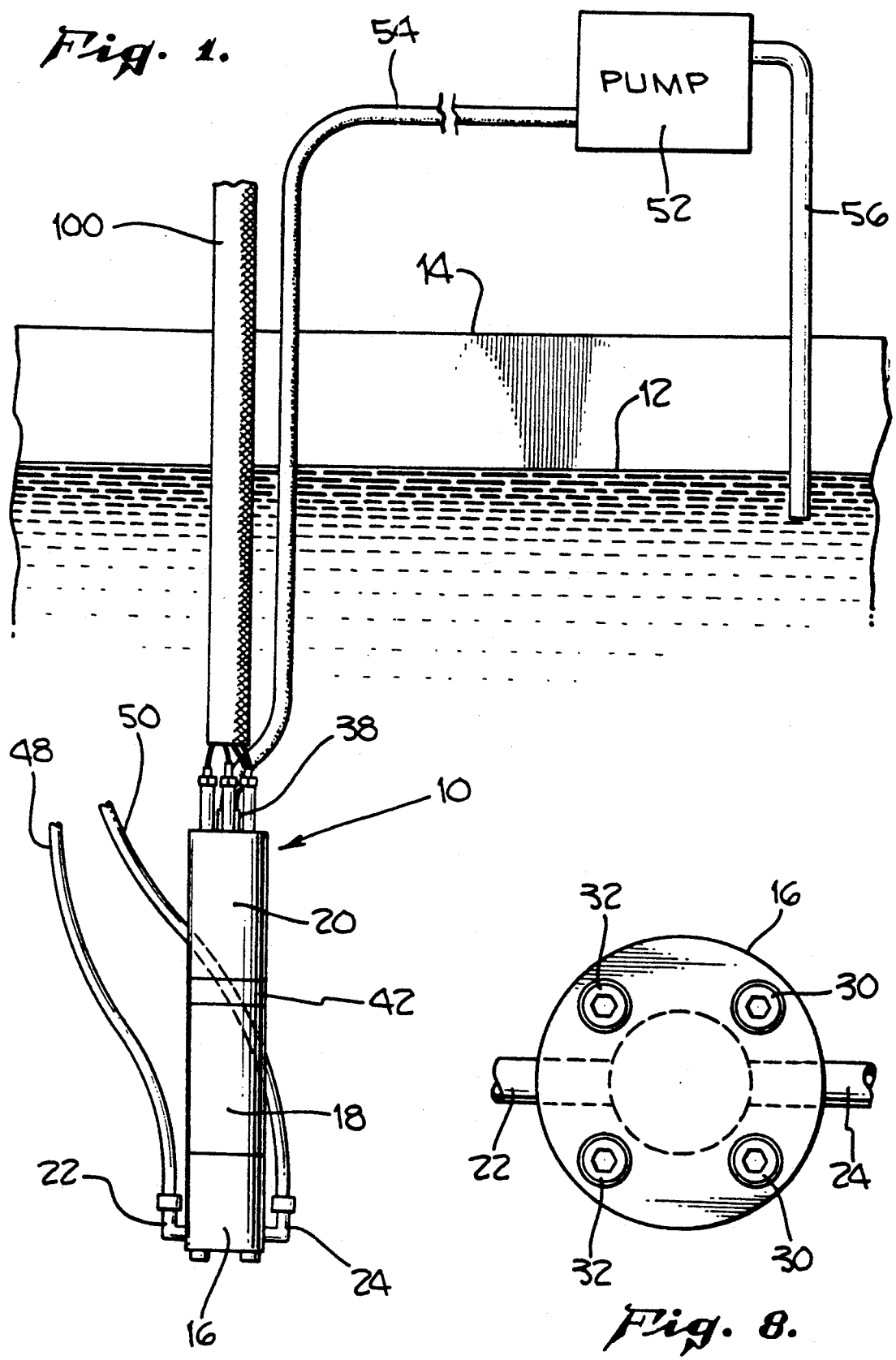

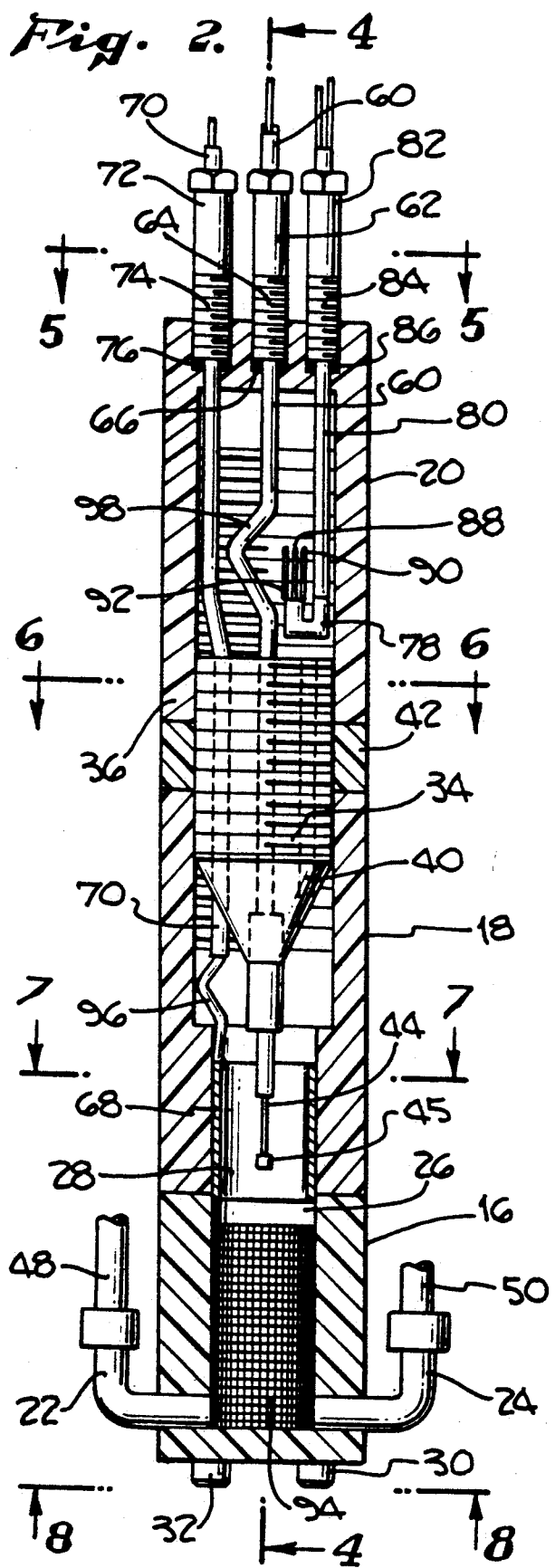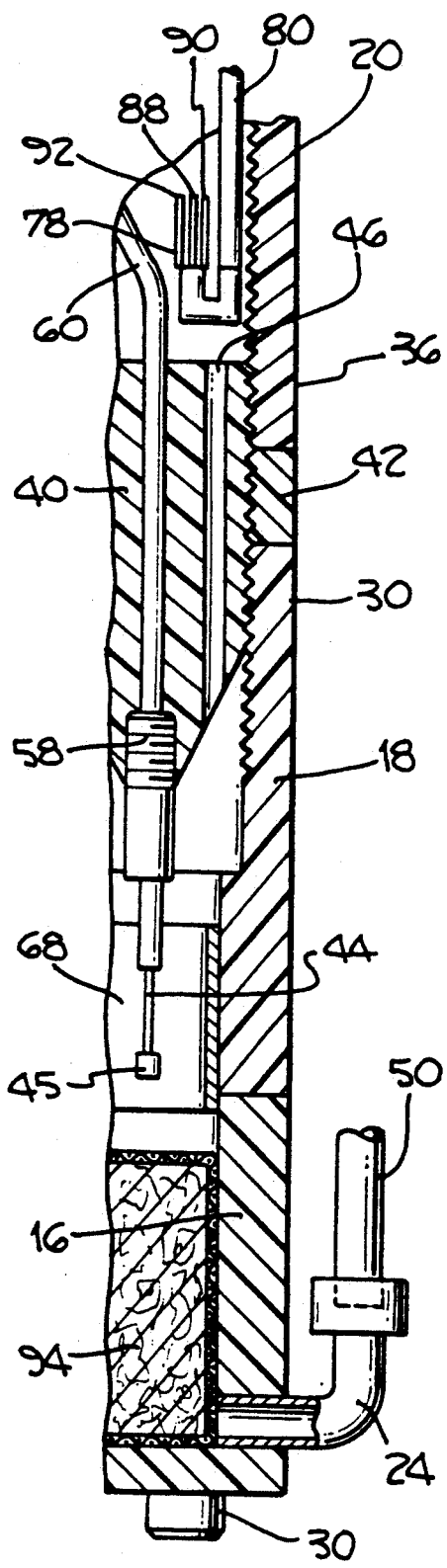

IN-TANK ELECTROCHEMICAL SENSOR

BACKGROUND OF THE INVENTION

1. Field of the Invention

The present invention relates generally to electrochemical sensors which are designed for use in measuring and monitoring electrochemical properties of liquids. More particularly, the present invention relates to an electrochemical sensor which is adapted for use in monitoring liquids using DC and AC voltammetric techniques.

2. Description of Related Art

U.S. Pat. No. 4,631,116, assigned to the present common assignee, discloses a method for monitoring the minor constituents which are present in plating bath solutions which affect plating deposit properties. The method involves applying a predetermined DC potential to a working electrode positioned within the plating bath solution. The DC potential is determined with respect to a reference electrode. A constant AC signal is superimposed on the DC potential. The DC potential is varied at a predetermined rate over a predetermined range which includes potentials which plate and strip the plating deposits.

The AC current of the applied AC signal is measured between the working electrode and a counter-electrode positioned within the plating bath solution as the DC potential is varied over the predetermined range. The measurement of the AC current in relation to varying DC potential is expressed as in AC current spectra or fingerprint. By optimizing all AC and DC measurement variables, spectra are obtained which contain fine structure and which enable the monitoring of minor plating bath constituents which affect plating deposit properties.

In order to conduct the delicate DC and AC voltammetric measurements in accordance with the above procedure, it is important that the three electrodes (reference, working and counter) be shielded from hydrodynamic and electrical interference from the plating bath. Further, it is important that the electrodes be positioned within the sensor apparatus in a manner which allows continuous and uniform passage of plating bath solution into contact with the electrodes. This requirement is necessary to ensure that the plating bath solution to which the electrodes are exposed is an accurate reflection of overall conditions within the plating bath.

In many large scale production facilities, it would be desirable to have a rugged electrochemical sensor which can withstand continual rough treatment while still providing the extremely accurate measurements mentioned above. The sensor should also be easily assembled and disassembled to allow cleaning and inspection. Further, the sensor should be constructed so that different electrodes may be changed into and out of the sensor to allow measurement of a variety of electrochemical properties in many different types of liquids.

As is apparent from the above, there presently is a need for multi-purpose sensor devices which are rugged enough to withstand commercial and industrial scale operations while at the same time providing for continual nonturbulent flow of solution into contact with the sensor electrodes in order to provide accurate electrochemical analysis of a variety of liquids.

SUMMARY OF THE INVENTION

In accordance with the present invention, an electrochemical sensor is provided which is especially well-suited for use in the AC-DC voltammetric electrochemical analysis of liquids. The electrochemical cell includes a cell assembly which is made up of a liquid flow control chamber, a sensing chamber and a liquid exit chamber. All three of the chambers include inlets and outlets. The liquid flow control chamber outlet is connected to the sensing chamber inlet to provide for flow of the liquid being measured from the liquid flow chamber into the sensing chamber. The sensing chamber is, in turn, connected to the liquid exit chamber to provide for flow of liquid from the sensing chamber into the liquid exit chamber.

In accordance with the present invention, a working electrode and a counter-electrode are located within the sensing chamber. A reference electrode is located within the liquid exit chamber. Liquid is transported through all three chambers by a pump. The pump transports liquid from the liquid flow control chamber inlet through the apparatus and out through the liquid exit chamber outlet. As a further feature of the present invention, a flow damper associated with the liquid flow control chamber is provided to ensure controlled hydrodynamic flow through the sensing chamber.

The electrochemical sensor in accordance with the present invention is a relatively simple and efficient device which is well-suited for use in making electrochemical measurements of a wide variety of liquids. The device is especially well-suited for those situations where extremely accurate AC and/or DC measurements are required. The sensor is further well-suited for use in environments, such as plating bath solutions, wherein the solution is typically turbulent. The electrochemical sensor of the present invention is easily disassembled for inspection, cleaning, and replacement of electrodes. As a result, the sensor assembly may be quickly and conveniently adapted for different electrochemical measurements by disassembling the device and changing the electrodes.

As a further feature of the present invention, the chambers of the sensor are cylindrical in shape and made from non-conductive materials. The non-conductive materials help shield the electrodes from outside electrical disturbances and the cylindrical shape facilitates construction, increases the durability of the sensor and provides a strong structure for protecting the electrodes during normal abuse typically experienced in the commercial production and industrial environment. In addition, the annular cell geometry guarantees uniform current distribution and helps to make the AC and DC measurements robust and accurate.

The above-discussed and many other features and attendant advantages of the present invention will become better understood by reference to the following detailed description of the preferred embodiments when taken in conjunction with the accompanying drawings.

BRIEF DESCRIPTION OF THE DRAWINGS

FIG. 1 is a side view of a preferred exemplary electrochemical sensor in accordance with the present invention showing the sensor immersed in a plating bath.

FIG. 2 is a detailed side sectional view of the electrochemical sensor shown in FIG. 1.

FIG. 3 is a partial side sectional view of the preferred exemplary sensor showing the lower portion of the sensor including the threaded engagement of the sensing chamber with the liquid exit chamber.

FIG. 8 is a sectional view of FIG. 2 taken in the 8—8 plane.

DETAILED DESCRIPTION OF THE PREFERRED EMBODIMENTS

A preferred exemplary electrochemical sensor in accordance with the present invention is shown generally at 10 in FIG. 1. The electrochemical sensor 10 is shown immersed in a plating bath solution 12 which is contained within a plating bath tank 14. Although the electrochemical sensor 10 is well-suited for use in the electrochemical analysis of plating baths, in accordance with the procedures disclosed in previously mentioned U.S. Pat. No. 4,631,116, it will be understood by those skilled in the art that the electrochemical sensor 10 may be used to measure electrochemical properties of a wide variety of liquids.

Figure 4:
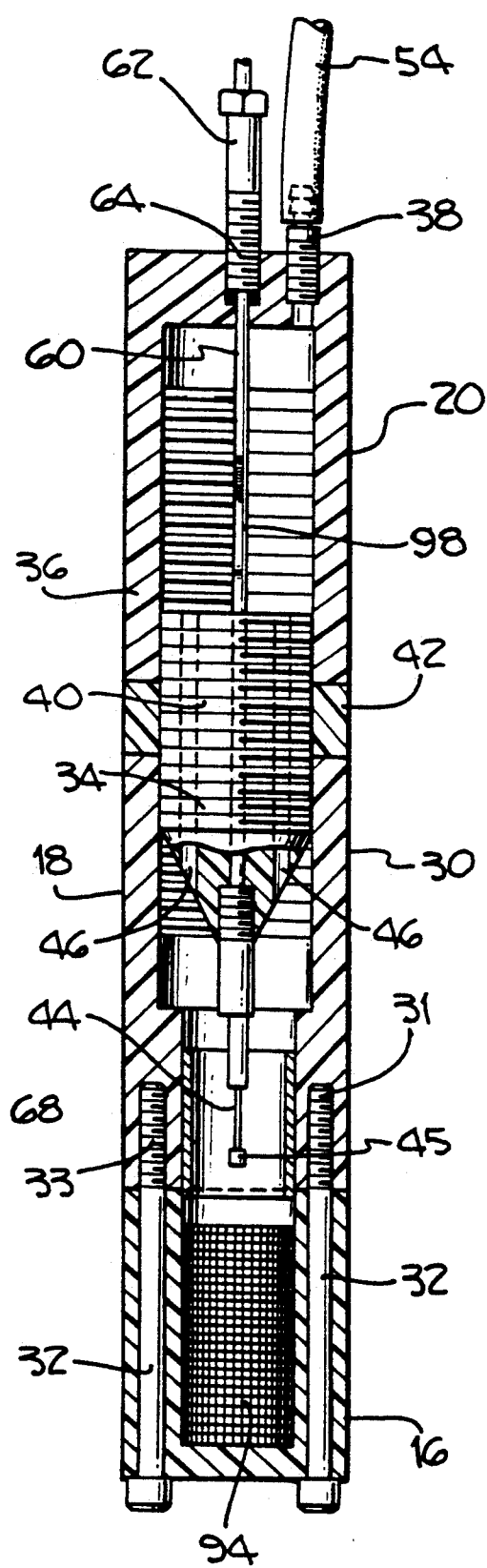
FIG. 4 is a sectional view of FIG. 2 taken in the 4—4 plane.

The electrochemical sensor 10 includes a cell assembly which is made up of a liquid flow control chamber 16, a sensing chamber 18 and a liquid exit chamber 20. As best shown in FIGS. 2 and 8, the liquid flow control chamber 16 includes inlets 22 and 24 through which liquid enters the sensor. The liquid flow control chamber 16 also has an outlet 26 through which the liquid flows from the liquid flow control chamber 16 into the sensing chamber 18. The sensing chamber 18 includes an inlet 28 through which liquid enters the sensing chamber 18 and an outlet portion 34 through which the liquid exits the sensing chamber 18. As best shown in FIGS. 4 and 8, the liquid flow control chamber 16 is connected to the sensing chamber 18 by way of bolts 30 and 32 which are screwed into the sensing chamber as shown at 31 and 33, respectively.

Figure 6:
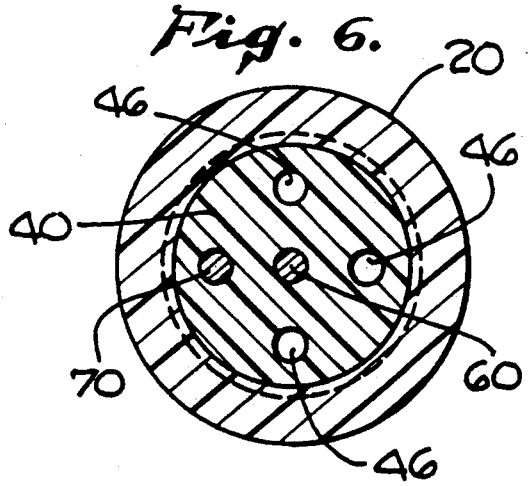
FIG. 6 is a sectional view of FIG. 2 taken in the 6—6 plane.

The liquid exit chamber 20 includes an inlet portion 36 and an outlet portion 38 (as best shown in FIG. 4) through which liquid exits the sensor 10. The sensing chamber outlet portion 34 is connected to the liquid exit chamber inlet portion 36 by way of a threaded insert 40 (see FIG. 3). The threaded insert 40 engages threads on the outlet portion of the sensing chamber 34 and the inlet portion of the liquid exit chamber 36. An adjustment ring 42 is provided for allowing the insert 40 to be moved relative to the sensing chamber 18 and liquid exit chamber 20 in order to provide desired positioning of the working electrode 44 within the sensing chamber 18. The threaded insert 40 includes liquid pass-through channels 46 through which plating bath solution flows from the sensing chamber 18 to the liquid exit chamber 20 (see FIGS. 3 and 6).

As shown in FIG. 1, tubes 48 and 50 are connected to the inlets 22 and 24 respectively. These tubes extend upward from the inlets 22 and 24 in order to prevent bubbles from entering the liquid flow control chamber 16. In addition, the tubes 48, 50 tend to reduce the turbulence in the liquid prior to entry into the inlets 22 and 24. The length of tubes 48 and 50 will depend upon the degree of turbulence present in the plating bath solution 12. For baths which are relatively non-turbulent, the tubes 48 and 50 may be eliminated, if desired.

Referring to FIG. 1, a suction pump 52 is provided for pumping plating bath solution into the sensor 10 by suction through tubes 48 and 50, up through the sensor 10 and out through outlet 38. Pump tube 54 is used to connect the suction inlet for pump 52 to the liquid exit chamber outlet 38. Tube 56 is connected to the pump outlet and provides for the return of plating bath solution back to the tank 14.

The walls of the liquid flow control chamber 16, sensing chamber 18 and liquid exit chamber 20 are made from a non-electrically conductive material, which is preferably a plastic, such as a polytetrafluoroethylene. Other non-conductive plastics or materials may be used provided that they are inert with respect to the particular solution in which they are to be immersed and are structurally relatively strong. The materials also should not include anything which might adversely affect the electrochemical measurements being made between the electrodes. In addition, the plastic material should be amenable to molding or machining so that the various structures required for the three chambers can be formed.

Figure 5:
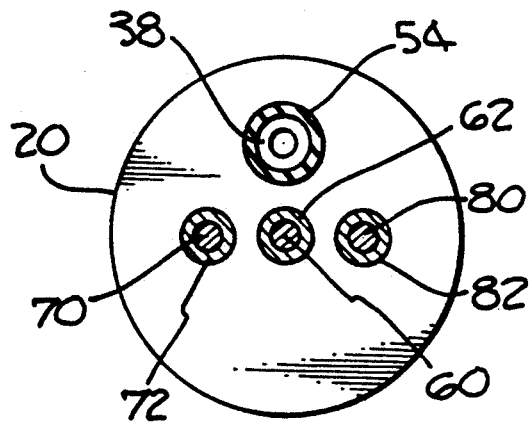
FIG. 5 is a sectional view of FIG. 2 taken in the 5—5 plane.

As best shown in FIG. 3, the working electrode 44, optionally with an insulating tip 45, is mounted to insert 40 by way of threads 58. An insulated working electrode connection wire 60 passes up through the insert 40 and exits through bushing 62 which is screwed into the top of the liquid exit chamber 20 as shown at 64. An O-ring 66 is provided to ensure a tight seal. In addition, as best shown in FIG. 5, the insulated wire 60 fits snugly within bushing 62.

Figure 7:
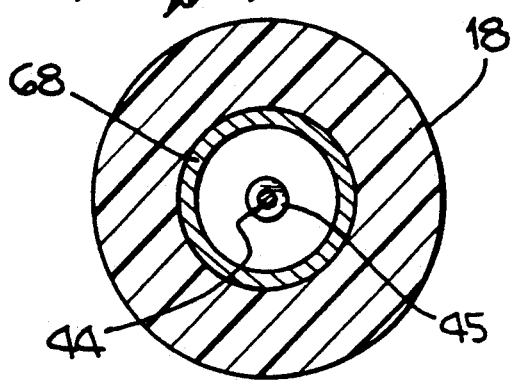
FIG. 7 is a sectional view of FIG. 4 taken in the 7—7 plane.

As best shown in FIG. 7, counter-electrode 68 is a cylindrical electrode which surrounds the working electrode 44. The counter-electrode 68 is connected to wire 70 which extends up through the insert 40 and exits through counter-electrode bushing 72. The bushing 72 is screwed into the top of the liquid exit chamber 20 as shown at 74 with O-ring 76 being provided to ensure a leak-proof seal.

A reference electrode is provided as shown at 78. The reference electrode 78 is located in the liquid exit chamber 20. If desired, the reference electrode may be located in the sensing chamber 18. The reference electrode 78 is connected to reference electrode wire 80 which extends up through the liquid exit chamber 20 and exits the sensor through bushing 82. The bushing 82 is screwed into the top of the liquid exit chamber 20 as shown at 84 with O-ring 86 also being provided to ensure a tight, leak-proof seal. The reference electrode arrangement can be a combination of one or more electrodes. A three-electrode arrangement is shown in FIG. 4.

The working electrode 44, counter-electrode 68 and reference electrode 78 are made from conventional materials typically used in electrode systems which are designed to measure sub-milliampere electrical currents. The working electrode 44 is preferably made from platinum or other electrode metal which is capable of providing stable measurements. The counter-electrode 68 is also preferably made from platinum foil or other suitable material. The reference electrode 78 is made up of a central electrode 88 which is surrounded by supplemental electrodes 90 and 92. This reference electrode configuration ensures accurate measurements. Standard saturated calomel electrodes are not acceptable for use as reference electrodes. Platinum is also the preferred material for the reference electrode. Other noble materials such as gold or palladium may also be used.

In accordance with the present invention, the liquid flow control chamber 16 may also include flow damper means such as glass felt or screen 94. Glass felt or any other inert fibrous matrix or mesh material may be used to reduce the turbulence of liquid entering the liquid flow control chamber 16 provided that the material is capable of dampening and substantially eliminating any turbulence which may be present in the liquid entering into the sensor 10 through inlets 22 and 24. The density of the glass felt or porosity of other damping materials may be varied depending upon the size of the sensor and the degree of turbulence in the liquid as it enters the assembly through inlets 22 and 24. Preferably, the density or porosity of the damping media is sufficient to substantially eliminate any turbulence in the liquid prior to contact with the working electrode 44. At the same time, the material should not be so dense that it overly restricts the flow of liquid into the sensing chamber 18.

The counter-electrode wire 70 preferably includes a flexible joint 96. This flexible joint protects the alignment of the counter-electrode 68 with respect to the working electrode 44 when the counter-electrode lead wire 70 is repositioned. Likewise, the working electrode wire 60 preferably includes a flexible joint 98 which protects the alignment of the working electrode when the working electrode lead wire is repositioned.

In operation, the sensor 10 is immersed in a plating bath or other solution to be analyzed as shown in FIG. 1. Solution is drawn into the sensor through tubes 48 and 50 by pump 52. The rate at which liquid is drawn into the sensor is limited to ensure that the turbulence dampening capabilities of the glass felt 94 are not exceeded and to ensure non-turbulent flow of liquid past the electrodes 44, 68 and 78. The various electrode wires 60, 70 and 80 are passed out of the tank within an appropriate shielding tube 100 and connected to measurement equipment designed for making sub-milliampere electrochemical measurements. Exemplary electrochemical analysis methods and equipment to which the sensor of the present invention is connected are described in U.S. Pat. No. 4,631,116 which has been previously mentioned. The contents of this patent is hereby expressly incorporated by reference.

Both the exterior and interior surfaces of the liquid flow control chamber 16, sensing chamber 18 and liquid exit chamber 20 are cylindrical in shape. The cylindrical shape for the interior of the chambers is preferred because it tends to reduce the chance of turbulence being generated in the sensor as the liquid passes through the three chambers. Also, it permits an annular electrode configuration, ensuring uniform distribution of current, which improves stability and the accuracy of the measurements. The length of the sensor in accordance with the present invention may be varied from a few centimeters up to a meter or more depending upon the particular electrochemical properties being measured and the type of liquid being passed through the sensor. Likewise, the diameter of the sensor may be varied from 1 centimeter up to 10 centimeters or more.

The sensor 10 may be easily disassembled for cleaning, inspection or replacement of electrodes by removing bolts 30 and 32 and unscrewing the liquid flow control chamber 16 from sensing chamber 18. Next, the sensing chamber 18 and liquid exit chamber 20 can be disengaged by unscrewing them from their threaded engagement with insert 40. The working electrode 44 and counter electrode 68 should be removed from the assembly before the liquid exit chamber 20 is unscrewed from insert 40 to prevent possible damage to the electrodes and associated wires due to twisting of the wires as the liquid exit chamber 20 is turned relative to the insert 40.

Having thus described exemplary embodiments of the present invention, it will be understood by those skilled in the art that the within disclosures are exemplary only and that the present invention is only limited by the following claims.

We claim:

1. An electrochemical sensor adapted for use in the electrochemical analysis of liquids, said electrochemical cell comprising:
   a cell assembly comprising a liquid flow control chamber, a sensing chamber and a liquid exit chamber wherein said liquid flow control chamber comprises an inlet and an outlet and said liquid exit chamber comprises an inlet and an outlet;
   first connection means for connecting said liquid flow control chamber outlet to said sensing chamber inlet to provide for flow of liquid from said liquid flow control chamber into said sensing chamber;
   second connection means for connecting said sensing chamber outlet to said liquid exit chamber inlet to provide for flow of liquid from said sensing chamber into said liquid exit chamber;
   a working electrode located within said sensing chamber;
   a counter-electrode located within said sensing chamber;
   a reference electrode located within said liquid exit chamber or within said sensing chamber;
   pump means for transporting said liquid through said cell assembly from said liquid flow control chamber inlet to said liquid exit chamber outlet; and
   flow damper means for controlling the flow of said liquid through said liquid flow control chamber so that the liquid entering said sensing chamber is free of turbulence.

2. An electrochemical sensor according to claim 1 wherein said cell assembly further comprises:
   working electrode connection means for electrically connecting said working electrode to an electrical measurement device located external to said electrochemical cell;
   counter-electrode connection means for electrically connecting said counter-electrode to an electrical measurement device located external to said electrochemical cell; and
   reference electrode connection means for electrically connecting said reference electrode to an electrical measurement device located external to said electrochemical cell.

3. An electrochemical sensor according to claim 1 wherein said flow damper means comprises gas entry inhibitor means for preventing the entry of gas into said liquid flow control chamber.

4. An electrochemical sensor according to claim 1 wherein said flow damper means comprises a mesh body located within said liquid flow control chamber through which said liquid flows as it passes through said liquid flow chamber from said inlet to said outlet.

5. An electrochemical sensor according to claim 3 wherein said flow damper means comprises a mesh body located within said liquid flow control chamber through said liquid flows as it passes through said liquid flow chamber from said inlet to said outlet.

6. An electrochemical sensor according to claim 1 wherein said counter-electrode is cylindrical in shape and wherein said working electrode is located within said cylindrical shape of said cylindrical counter-electrode.

7. An electrochemical sensor according to claim 1 wherein said second connection means comprises a threaded connection between said sensing chamber outlet and said liquid exit chamber inlet.

8. An electrochemical sensor according to claim 1 wherein said sensing chamber is made from electrically non-conductive material.

9. An electrochemical sensor according to claim 8 wherein said liquid flow control chamber is made from electrically non-conductive material.

10. An electrochemical sensor according to claim 8 wherein said liquid exit chamber is made from electrically non-conductive material.

11. An electrochemical sensor according to claim 1 wherein said liquid flow control chamber is cylindrical in shape.

12. An electrochemical sensor according to claim 11 wherein said sensing chamber is cylindrical in shape.

13. An electrochemical sensor according to claim 12 wherein said liquid exit chamber is cylindrical in shape.

14. A method for sensing the electrochemical properties of a liquid comprising the steps of:
   flowing said liquid into a liquid flow control chamber;
   removing turbulence present in said liquid in said flow control chamber to provide a turbulence free liquid;
   passing said turbulence free liquid from said liquid flow control chamber into a sensing chamber;
   contacting said turbulence free liquid in said sensing chamber with a working electrode and a counter-electrode;
   passing said turbulence free liquid from said sensing chamber into a liquid exit chamber;
   contacting said turbulence free liquid in said exit chamber with a reference electrode; and
   sensing one or more electrochemical properties of said turbulence free liquid between said working electrode, counter-electrode and said reference electrode.

15. A method for sensing the electrochemical properties of a liquid according to claim 14 wherein said liquid is plating bath liquid.

16. A method for sensing the electrochemical properties of a liquid according to claim 14 wherein said liquid is passed through a mesh body in said liquid flow control chamber to provide removal of turbulence from said liquid to provide said turbulence free liquid.

17. A method for sensing the electrochemical properties of a liquid according to claim 14 wherein said step of removing turbulence from said liquid includes the step of removing gas from said liquid prior to flowing said liquid into said liquid flow control chamber.

18. A method for sensing the electrochemical properties of a liquid according to claim 14 wherein said step of sensing an electrochemical property of said liquid comprises the steps of:
   applying a DC potential between said working electrode and said counter-electrode;
   applying an AC signal superimposed on the DC potential between said working electrode and said counter-electrode; and
   measuring the AC current or potential of said AC signal between said working electrode and said counter-electrode.

* * * * *